United States Patent [19]

Lapetina et al.

[11] Patent Number: 4,540,981

[45] Date of Patent: Sep. 10, 1985

[54] METHOD AND APPARATUS FOR DETECTING THE PRESENCE OF LIQUID

[75] Inventors: Robert A. Lapetina; Howard P. Jones, both of Salt Lake City, Utah

[73] Assignee: Edo Western Corporation, Salt Lake City, Utah

[21] Appl. No.: 316,506

[22] Filed: Oct. 29, 1981

[51] Int. Cl.³ .................... G08B 21/00; G01F 23/00
[52] U.S. Cl. ................ 340/618; 73/290 V; 310/321; 340/621
[58] Field of Search ............ 340/618, 619, 621, 620, 340/617; 73/304 C, 290 V; 324/61 P, 61 QS; 128/715; 310/321

[56] References Cited

U.S. PATENT DOCUMENTS

| 3,013,256 | 12/1961 | Damast | 340/621 X |
| 3,050,720 | 8/1962 | Rich | 340/621 |
| 3,163,843 | 12/1964 | Dieckamp | 73/290 V |
| 3,256,738 | 6/1966 | Giacomo et al. | 73/290 V |
| 3,266,311 | 8/1966 | Andreasen et al. | 73/290 V |
| 3,283,181 | 11/1966 | Johanson | 128/715 |
| 4,008,613 | 2/1977 | Myers | 340/617 X |
| 4,107,994 | 8/1978 | Sogo | 73/290 V |
| 4,314,242 | 2/1982 | Kuru et al. | 340/621 |

FOREIGN PATENT DOCUMENTS

| 2949162 | 6/1979 | Fed. Rep. of Germany | 73/290 V |
| 2054853 | 2/1981 | United Kingdom | 73/290 V |

Primary Examiner—James L. Rowland
Assistant Examiner—Daniel Myer
Attorney, Agent, or Firm—Thorpe, North & Western

[57] ABSTRACT

Method and apparatus for detecting the presence of liquid in a container includes an elongate rod (or other vibratory element) which extends into the container to contact liquid when a certain amount of liquid is present, a piezo-electric element coupled to the rod on the exterior of the container to cause the rod to vibrate in response to electrical signals and to produce electrical signals indicative of the amplitude of vibration of the rod, and circuitry for producing a utilization signal when the electrical signals produced by the piezo-electric element indicate that the amplitude and duration of vibrations of the rod are below some threshold level. Such vibrations fall below the threshold level when the rod contacts liquid in the tank and so production of the utilization signal is an indication that liquid in the container has reached a certain level.

21 Claims, 2 Drawing Figures

METHOD AND APPARATUS FOR DETECTING THE PRESENCE OF LIQUID

BACKGROUND OF THE INVENTION

This invention relates to a method and apparatus for detecting liquids in a container in which all electrical conductors may be placed exterior to the container.

Conventional methods of detecting the presence of fuel in aircraft fuel tanks involve placement of capacitive sensors within the tanks. When fuel surrounds the sensors, their capacitance changes to indicate that a certain fuel level (the level of placement of the sensors) has been reached. Of course, electrical conductors extend into the fuel tank to connect to the capacitive sensors.

The above-described method presented little safety problems when aircraft fuel tanks were carried within all metal wings since the wings would act as electrostatic shields to prevent lightning, for example, from reaching the interior of the fuel tanks. However, with the advent of the use or proposed use of non-metallic material, such as graphite, in wing construction, the "electrostatic shield" feature was lost. With this construction, lightning might penetrate the non-metallic material to reach electrical conductors of fuel measuring circuitry and the electric charge of such lightning could thus be conducted to the interior of the fuel container to cause an explosion.

In addition to the safety problem above discussed, existing fuel sensing systems are difficult to service and repair, at least as to that portion which is located within the fuel tank. This difficulty could be reduced by placing as much of the fuel sensing system as possible exterior to the tank.

SUMMARY OF THE INVENTION

It is an object of the invention to provide a new and improved system for detecting the presence of liquid.

It is also an object of the invention to provide such a system which is simple in construction and easy to maintain and service.

It is another object of the invention to provide a safe system for sensing the presence of fuel or other volatile liquid in a container.

It is an additional object of the invention to provide a system for detecting liquid in a container in which the system includes electrical circuitry which is disposed exterior to the container.

It is a further object of the invention to provide such a system which is reliable in operation in a variety of environmental conditions.

The above and other objects of the invention are realized in a specific illustrative embodiment of a system for detecting liquid in a container wherein the system includes an elongate rod (or other vibratory element such as a diaphragm, piston, etc.) mounted to extend into or be exposed to the interior of the container, an energizing element coupled to the rod but disposed outside the container for causing the rod to vibrate, a detecting element, which may include the energizing element, for detecting the amplitude of the vibrations of the rod, and signal producing circuitry for producing an output signal when the amplitude of the vibrations fall below some predetermined level. This signal is indicative that liquid is present about the rod thereby dampening its vibrations, and thus that the liquid has reached the level of the rod in the tank. Since no electrical conductors extend into the container, no electrical charges can be conducted to the interior of the container to cause explosions (if the liquid were explosive).

Advantageously, the energizing element stimulates the rod to vibrate over a range of frequencies which encompasses the resonant frequency of the rod. With this feature, even though the resonant frequency of the rod may change (with temperature for example), it is assured that the energizing element will sweep through a frequency which will stimulate the rod to vibrate at its resonant frequency.

BRIEF DESCRIPTION OF THE DRAWINGS

The above and other objects, advantages and features of the invention will become apparent from a consideration of the following detailed description presented in connection with the accompanying drawings in which.

DETAILED DESCRIPTION

Figure 1:
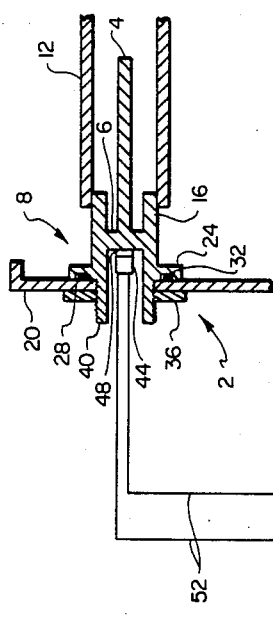
FIG. 1 shows a cross-sectional view of a liquid probe with accompanying circuitry made in accordance with the principles of the present invention.
Figure 1:
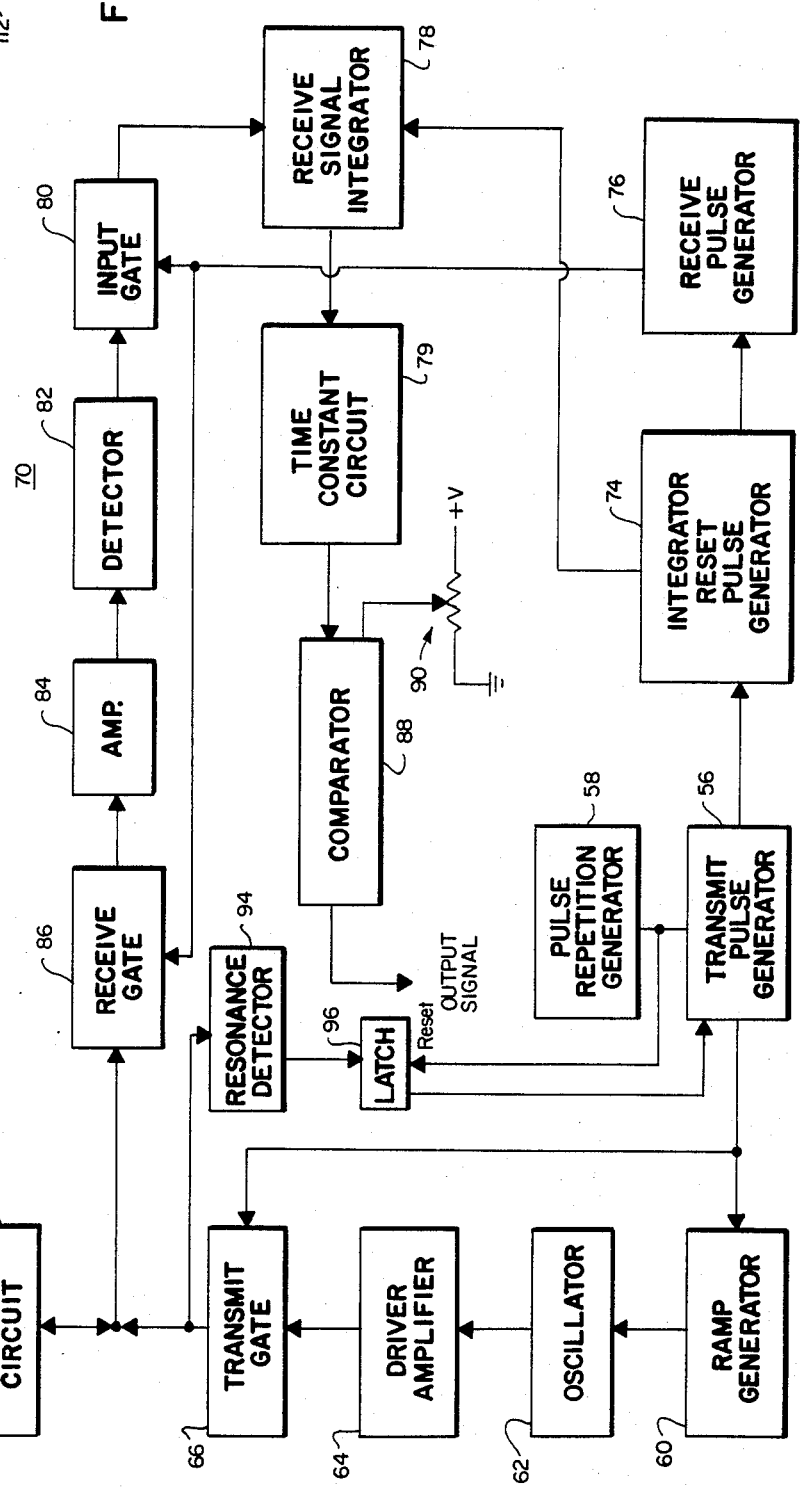

An illustrative embodiment of the present invention is shown in FIG. 1 to include a probe 2 which has an elongate rod 4 extending from a platform 6 of a base 8 into a tube 12 which is connected to a liquid container. When the liquid in the container reaches a certain level, it flows into the tube 12 and about the rod 4. The tube 12 is fitted about a tubular rim 16 which projects forwardly of the base 8 and about a portion of the rod 4. The tube 12 is joined to the rim 16 and held in place by a suitable fuel resistant sealing connection, such as an adhesive or clamp. Advantageously, the probe 2 is made of aluminum or aluminum alloy, although other materials could also be used.

An alternative arrangement for using the probe 2 involves mounting the probe directly on a wall 20 of the liquid container so that the rod 4 projects into the interior of the container and so that a portion of the base 8 extends through an opening in the wall 20 to a location exterior to the container. In such case, the liquid conveying tube 12 would not be used. In both arrangements, the objective is to place the probe in a position to contact liquid when the liquid reaches a certain level in a holding container. The probe may be mounted in any attitude, for example horizontally as shown, vertically, or at any other angle of convenience. (Of course, as will become clear later, the probe is also usable to simply detect the presence or absence of liquid generally without being concerned with the level of liquid in a container.)

The base 8 of the probe includes an outwardly projecting lip 24 having a groove 28 in one side thereof for receiving and holding a sealing ring 32. The lip 24, groove 28 and sealing ring 32 are provided to seal the base 8 in place in the opening in the wall 20 and prevent liquid from flowing out the opening. The probe 2 is secured on the wall 20 screwing a nut 36 onto a threaded tubular portion 40 of the base 8 which projects rearwardly of the rod 4.

Figure 2:
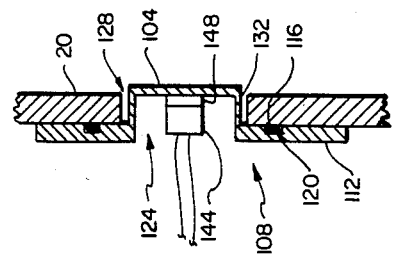
FIG. 2 shows a cross-sectional view of another embodiment of a probe in which a vibratory diaphram is used.

Although a specific structure for the probe 2 has been described, it will be apparent that a variety of other configurations could be used so long as some vibratory element were arranged to be exposed to the interior of the container (or the tube 12), with a portion of the base 8 being exposed to the outside. For example, FIG. 2 shows a probe which utilizes a vibratory diaphragm 104 disposed to be generally flush with the interior surface of the container wall 20. The diaphragm 104 is part of a plate 108 (made, for example, of aluminum) which includes a base portion 112 having a groove 116 in one side thereof for receiving and holding a sealing ring 120. The base portion 112 includes an opening 124 which is smaller than the opening 128 over which the plate 108 is installed. Extending from the inner edge of the base portion 112 which defines the opening 124 generally at a right angle to the plane of the base portion is a collar 132. The diaphragm 104, which is generally planar, extends inwardly from the outer rim of the collar 132 to cover the opening 124. The collar portion 132 of the plate 108 is made as thin as possible, while maintaining structural integrity, to provide acoustical isolation between the diaphragm 104 and the thicker base portion 112. This will minimize the effect of the mounting method on the vibrations of the diaphragm. The plate 108, when installed as shown, covers the opening 128 in the container to expose the diaphragm 104 to the interior of the container.

Mounted on the backside of the diaphragm 104 is an electromechanical driver 144 joined by way of a gasket 148 to the diaphragm. The electromechanical driver 144, which might illustratively be a piezoelectric crystal, responds to electrical signals by mechanically vibrating to, in turn, cause the diaphragm 104 to vibrate. This function, and the function of the gasket 148 and diaphragm 104 are similar to those of the probe 2 of FIG. 1 and of an electromechanical driver 44 and gasket material 48 of FIG. 1 which will next be described.

Referring again to FIG. 1, there is shown mounted in the hollow of the tubular member 40 on the side of the platform 6 opposite that from which the rod 4 extends an electro-mechanical driver 44 for vibrating in response to receipt of an electrical oscillatory signal, and for producing an electrical oscillatory signal when caused to vibrate mechanically. The driver 44 may be a piezo-electric crystal or a magnetostrictive device. Mounted between the driver 44 and the platform 6 is a gasket material 48. Gasket material with a coefficient of expansion between that of the platform 6 and that of the driver 44 is selected so that expansion or contraction of the platform material 6 will be less likely to break or damage the driver 44. For a platform material of aluminum and a piezoelectric crystal driver 44, a gasket material of a composite of fiberglass and epoxy has been found suitable. The composite serves to both protect the driver 44 and transmit mechanical vibrations between the driver and rod 4. An adhesive on both sides of the gasket serves to attach it to the driver and to the platform. The composite material is a combination of glass cloth, or oriented nonwoven parallel aligned glass fibers, epoxy-resin and a plastic thermosetting sheet, commonly designated type GEE per M1L-P-18177. This material is typically used for printed circuit boards.

The driver 44 is electrically coupled by cables 52 to an impedance matching circuit 54 which is provided, as the name indicates, to match the impedance of the cables 52 with that of remaining circuitry of the drawing, to be described momentarily. The circuit 54 is needed only if long connecting cables 52 are employed.

The circuitry for producing an oscillatory signal for application to the driver 44 includes a transmit pulse generator 56 which produces a fixed-length "transmit" pulse each time it is triggered by a pulse repetition generator 58. The pulse repetition generator 58 might illustratively be an oscillator whose frequency determines the rate of production of the transmit pulses. The transmit pulse generator 56 might illustratively be a one-shot multivibrator.

The transmit pulses are applied to a ramp generator 60 and to a transmit gate 66. The ramp generator 60 produces either a linear ramp voltage output or an exponential ramp voltage output, in response to and for the duration of the "transmit" pulse. The ramp voltage is applied to an oscillator 62 which produces an oscillatory signal whose output signal frequency varies with the variation in the level of the ramp voltage. In this manner, an oscillatory signal is produced whose frequency varies over some predetermined range of frequencies. The purpose of this is to ensure that the oscillatory signal supplied to the driver 44 will sweep over the natural or resonant frequency of the rod, even if that natural frequency changes, for example, with temperature.

The output of the oscillator 62 is supplied to a driver amplifier 64 for amplifying the signal, and then is supplied via the transmit gate 66 to the impedance matching circuit 54. The transmit gate 66 assumes an "open" condition in response to the transmit pulse received from the transmit pulse generator 56, and remains open for the duration of the transmit pulse. When the transmit pulse terminates, the transmit gate 66 "closes" to prevent application of any signal to the circuit 54 (and also prevents application of any signal from the impedance matching circuit to the driver amplifier 64). The function of the transmit gate 66 is to present a high impedance to the driver 44 in the "receive" phase of the system (to be discussed momentarily) so as not to present a dampening load to the output of the driver. This could also be achieved by eliminating the gate 66, and providing a driver amplifier 64 which had a low output impedance when transmitting and a high impedance when not transmitting.

The above-described circuitry supplies an oscillatory signal to the driver 44 during a "transmit" phase of the system. The driver 44 is thus caused to oscillate to in turn cause the rod 4 to vibrate. After the "transmit" phase, the system enters a "receive" phase in which the amplitude of the vibrations of the rod 4 are measured. In particular, at the conclusion of a "transmit" phase when the oscillatory signal produced by the oscillator 62 is no longer supplied to the driver 44, the driver then produces an oscillatory electrical output signal whose amplitude is proportional to the amplitude of the vibrations of the rod 4. This output signal is supplied via the impedance matching circuit 54 to receive circuitry 70 to next be described.

The receive circuitry 70 includes an integrator reset pulse generator 74 which, in response to the trailing edge of the transmit pulse produced by the transmit pulse generator 56, produces a pulse which is applied to a receive pulse generator 76 and to a receive signal integrator 78 to reset the integrator. The receive pulse generator 76 is triggered by the trailing edge of the pulse produced by the reset pulse generator 74 to thereby produce a receive pulse which is applied to an imput gate 80 and a receive gate 86. The integrator reset pulse generator 74 and receive pulse generator 76 might illustratively be one-shot multivibrators.

The receive pulse opens receive gate 86 and input gate 80 for a time equal to the duration of the pulse. At the termination of the receive pulse, both gates assume a closed condition. The receive gate is opened just after conclusion of the transmit phase to allow application to an amplifier 84 of the oscillatory output signal produced by the driver 44. During the transmit phase, the receive gate is closed to prevent transmittal to the amplifier 84 of the signals produced by the oscillator 62.

The amplifier 84 amplifies the oscillatory output signal produced by the driver 44 and supplies it to a detector 82 which, in turn, rectifies the signal so that the voltage output is only one polarity. The rectifying function of the detector 82 may be either full wave or half wave.

The rectified output signal is supplied by the detector 82 via the input gate 80 to a receive signal integrator 78. The integrator 78 integrates the output signal during the receive phase, and holds and supplies to a time constant circuit 79 the accumulated charge until the integrator is reset by the pulse from the integrator reset pulse generator. The comparator compares this output with a predetermined, selectable voltage produced by a potentiometer 90, and produces an output signal indicative of whether the time constant circuit voltage level was higher or lower than the preselected level. Illustratively, the potentiometer will be set so that the voltage produced thereby will be higher than the time constant circuit signal level when the vibrations of the rod 4 are dampened by the presence of liquid for a time set by the charge time and decay time of the time constant circuit 79. In such case, the amplitude of vibrations will not be great so that the amplitude of the oscillatory output signal produced by the driver 44 will also not be great. Thus, the integrated signal level will not be great when the rod 4 is dampened and so, in such case, the time constant signal will "decay" to a level equal to the integrator output which will be less than the predetermined signal level. When no liquid is present about the rod 4, the vibrations of the rod will not be dampened and the amplitude of the oscillatory output signal produced by the driver 44 will be greater, and the integrated signal level will be greater thus causing the time constant circuit 79 to "charge" to a level greater than the predetermined level produced by the potentiometer 90. In this manner, a determination can be made as to whether or not liquid is present about the rod 4, i.e., if liquid is present, the time constant output signal will be less than the predetermined level and the comparator output signal will so indicate, and if liquid is not present, the time constant signal will be greater than the predetermined level and the comparator will similarly indicate that.

The receiver signal integrator 78 is a conventional circuit for integrating a rectified oscillatory signal, the time constant circuit 79 is a conventional resistor and capacitor combination for holding a charge which decays with time and the comparator 88 is a conventional comparator circuit.

The output signal from the comparator 88 could be used, for example, to turn off a liquid filling system automatically without having to oversee the filling operation. Such use would be especially desirable in the filling of aircraft fuel tanks with fuel.

During extreme operating temperatures for the probe 2, the resonant frequency of the piezo-electric crystal will shift considerably. Maximum received output from the crystal occurs if the oscillator frequency is the resonant frequency when the transmit pulse length terminates. With a fixed transmit pulse length, the received output will be reduced as the resonant frequency shifts with temperature. As a refinement to the system for improving performance over extreme temperatures and also to compensate for system component variability, an automatic resonance detector 94 is incorporated which determines when the resonant frequency of the crystal 44 is reached and then acts to terminate the transmit pulse. At frequencies near resonance, the magnitude and phase angle of the piezo-electric crystal impedance is changing radically. This creates a different loading condition for the output of the driver amplifier 64. By detecting either an amplitude change or a change in the current and voltage phase relationship of the driver amplifier output, a resonance condition can readily be detected. The output of the resonance detector sets a latch circuit 96 whose output is used to terminate the transmit pulse length. The latch circuit 96 remains in a "disabling" state until reset by an output logic level from the pulse repetition generator 58. This occurs just prior to the initiation of the next transmit pulse. The resonance detector 94 could be a conventional amplitude detector (if detecting amplitude shift) or a phase coincidence detector (if detecting current and voltage phase coincidence which indicates resonance).

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Apparatus for detecting the presence of liquid in a container, said apparatus comprising
    a vibratory element mounted so that a part thereof extends into the container and into contact with liquid if a certain amount of liquid is present, and another part is disposed exterior to the container,
    electro-mechanical means mechanically coupled to said another part of the vibratory element for vibrating in response to an electrical signal to thereby cause the element to vibrate,
    means for applying an electrical signal to said electro-mechanical means during intermittent transmit time phases, and including
        means for producing said electrical signal, and
        means for applying it to said electro-mechanical means to cause it to vibrate at a frequency which varies periodically over a range of frequencies which encompasses the resonant frequency of the vibratory element,
    means for detecting vibrations of the vibratory element during receive time phases which alternate with the transmit time phases, and for producing a first signal indicative of the amplitude of the vibrations, and
    means responsive to said first signal for producing a second signal when said vibrations are below a certain amplitude, indicating that liquid is present about the vibratory element dampening the vibrations.

2. Apparatus as in claim 1 wherein the container has an opening therein, and wherein said vibratory element includes a rod means having
    a base portion dimensioned for mounting on the container wall to cover the opening, and an elongate rod extending from the base portion into the container to contact liquid if a certain amount of liquid is present.

3. Apparatus as in claim 2 further comprising seal means disposed between the base portion and the container wall to prevent the flow of liquid thereby.

4. Apparatus as in claim 2 wherein said rod means is comprised of aluminum alloy.

5. Apparatus as in claim 1 wherein said container has an opening therein, and wherein said vibratory element includes
   a base plate for mounting on the container wall to cover the opening, said base plate having an aperture therein which generally coincides with the opening in the container and
   diaphragm means covering said aperture so as to be exposed to the interior of the container.

6. Apparatus as in claim 5 further comprising seal means disposed between the base plate and the container wall to prevent the flow of liquid thereby.

7. Apparatus as in claim 1 wherein said electro-mechanical means is a piezoelectric crystal.

8. Apparatus as in claim 1 wherein said electro-mechanical means is a magnetrostrictive device.

9. Apparatus for detecting the presence of liquid in a container, said apparatus comprising
   a vibratory element mounted so that a part thereof extends into the container and into contact with liquid if a certain amount of liquid is present, and another part is disposed exterior to the container,
   electro-mechanical means mechanically coupled to said another part of the vibratory element for vibrating in response to an electrical signal to thereby cause the element to vibrate,
   means for applying an electrical signal to said electro-mechanical means to cause it to vibrate,
   means for detecting vibrations of the vibratory element and for producing a first signal indicative of the amplitude of the vibrations,
   means responsive to said first signal for producing a second signal when said vibrations are below a certain amplitude, indicating the liquid is present about the vibratory element dampening the vibrations, and
   gasket means disposed between the electro-mechanical means and the vibratory element and having a coefficient of expansion between that of the electro-mechanical means and that of the vibratory element.

10. Apparatus as in claim 9 wherein said vibratory element is a rod means comprised of aluminum or aluminum-alloy, said electro-mechanical means is a piezoelectric crystal, and said gasket means is made of a composite of fiberglass and epoxy.

11. Apparatus as in claim 1 wherein the electrical signal applying means includes means for causing the vibratory element to vibrate at a frequency which varies continuously over the range of frequencies.

12. Apparatus as in claim 1 wherein the electrical signal applying means includes means for causing the vibratory element to vibrate at a frequency which varies step wise over the range of frequencies.

13. Apparatus for detecting the presence of liquid in a container, said apparatus comprising
   a vibratory element mounted so that a part thereof extends into the container and into contact with liquid if a certain amount of liquid is present, and another part is disposed exterior to the container,
   electro-mechanical means mechanically coupled to said another part of the vibratory element for vibrating in response to an electrical signal to thereby cause the element to vibrate,
   means for applying an electrical signal to said electro-mechanical means to cause it to vibrate,
   means for detecting vibrations of the vibratory element and for producing a first signal indicative of the amplitude of the vibrations,
   means responsive to said first signal for producing a second signal when said vibrations are below a certain amplitude, indicating that liquid is present about the vibratory element dampening the vibrations, and
   wherein said electrical signal applying means further includes
      oscillator means for producing an oscillatory signal whose frequency varies in response to variation in the amplitude of an input signal,
      means for supplying the oscillatory signal to the electro-mechanical means to cause it to vibrate, and
      means for producing an input signal for application to the oscillator means and for varying the amplitude of the input signal over some predetermined range.

14. Apparatus as in claim 13 wherein the electrical signal applying means includes means for causing the amplitude of the input signal to vary over a range to cause the oscillator to vary the frequency of the oscillatory signal over a range which encompasses the resonant frequency of the vibratory element.

15. Apparatus as in claim 13 wherein the electrical signal applying means further includes gate means coupled between the oscillator means and electro-mechanical means for intermittently opening to supply said oscillatory signal to said electro-mechanical means, and for alternately closing to block transmittal of signals to said oscillator means.

16. Apparatus as in claim 15 wherein the electrical signal applying means further includes means for producing a resonance signal when said vibratory element vibrates at its resonant frequency, and means for closing said gate means when said resonance signal is produced.

17. Apparatus as in claim 13 further including gate means coupled between the detecting means and the second signal producing means for intermittently opening to allow said first signal to be transmitted to said second signal producing means, and for alternately closing to block transmittal of signals to the second signal producing means.

18. Apparatus as in claim 1 wherein said detecting means comprises said electro-mechanical means which produces said first signal which is an oscillatory signal whose amplitude is proportional to the amplitude of vibration of the vibratory element.

19. Apparatus as in claim 18 wherein said second signal producing means comprises
   a comparator means for producing said second signal when the amplitude of the first signal is below some predetermined level,
   a detector means for rectifying said first signal, and
   an integrator means coupled to the detector means for integrating the rectified signal and for supplying the resultant integrated signal level to said comparator means for comparing with said predetermined level.

20. Apparatus as in claim 19 wherein said second signal producing means further comprises a time constant circuit means for accumulating the integrated signal levels and means for supplying the accumulated levels to said comparator means for comparing with said predetermined level.

21. A method of detecting the presence of liquid in a container comprising
(a) providing a vibratory element, a portion of which is exposed to the interior of the container and a portion of which is exterior to the container,
(b) stimulating that portion of the vibratory element which is exterior to the container during intermittent transmit time phases to cause the element to vibrate, said stimulating step including causing the frequency of vibration of the vibratory element to sweep over a range of frequencies which encompasses the resonant frequency of the vibratory element,
(c) detecting the amplitude of vibration of the element during receive time phases which alternate with the transmit time phases, and
(d) producing a signal indicative to the presence of liquid about the element when the amplitude of vibration of the element is below some predetermined level.

* * * * *